United States Patent [19]

Kitamura et al.

[11] Patent Number: 5,541,063
[45] Date of Patent: Jul. 30, 1996

[54] HUMAN INTERLEUKIN-3 RECEPTOR α SUBUNIT

[75] Inventors: Toshio Kitamura; Atsushi Miyajima, both of Palo Alto, Calif.

[73] Assignee: Schering Corporation, Kenilworth, N.J.

[21] Appl. No.: 133,038

[22] PCT Filed: Apr. 16, 1992

[86] PCT No.: PCT/US92/03026

§ 371 Date: Oct. 13, 1993

§ 102(e) Date: Oct. 13, 1993

[87] PCT Pub. No.: WO92/18628

PCT Pub. Date: Oct. 29, 1992

Related U.S. Application Data

[63] Continuation of Ser. No. 688,355, Apr. 19, 1991, abandoned.

[51] Int. Cl.$^6$ .................. C07K 14/705; C12N 15/12; C12N 1/19; C12N 1/21
[52] U.S. Cl. .................. 435/6; 435/7.2; 435/7.1; 435/64.1; 435/152.3; 435/320.1; 530/350; 536/23.5
[58] Field of Search ............... 435/6, 7.1, 7.2, 435/69.1, 252.3, 320.1; 530/350; 536/23.5

[56] References Cited

PUBLICATIONS

Hayashida et al, *P.N.A.S.* 87:9655–9659, Dec. 1990.
Kitamura et al, *J. Cell Physiol.* 140:323–334, 1989.
Itoh et al., *Science* 247:324–327, 19 Jan, 1990.
Sims et al., *P.N.A.S.* 86:8946–8950, Nov. 1989.
Shimuzu et al., *Nucl. Acid. Res.* 13(5):1505–1513 May 1985.
Goodwin et al., *Cell* 60:941–951, Mar. 1990.
Gearing et al., *EMBO J.*, vol. 8 (1989), pp. 3667–3676.
Gorman et al., *PNAS* vol. 87 (1990) pp. 5459–5463.
Gesper et al., *Blood*, 74 (8) (1989), pp. 2652–2656.
Uredal et al., *N Y Acad. Sci.* 554 (1989), pp. 167–176.
Reed et al., *Cell* 50 (1987), p. 667.
Lewin et al., *Science* 237 [no page No. given].
Burgman et al., *Nature* 319 (1986), pp. 226–230.
Yamamoto et al., *Nature* 319 (1986), pp. 230–234.
Kaczmarski et al., *Blood Rev.*, 5(3) (1991), pp. 193–203.
Kitamura et al., *Blood*, 80(1) (1992), pp. 84–90.
Kitamura et al., *Cell* 66 (6), Sep. 20, 1991, pp. 1165–1174.
Kuwaki et al., *Biochem. & Biophys. res. Comm.*, 161(1), May 30, 1989, pp. 16–22.

*Primary Examiner*—John Ulm
*Attorney, Agent, or Firm*—Stephen C. Macevicz; Edwin P. Ching

[57] ABSTRACT

The present invention relates to the isolation and cloning of the α-chain of the human IL-3 receptor, which, when expressed together with the β-chain of the human IL-3 receptor, forms a high affinity receptor for human IL-3. The invention further relates to a method for detecting agonists and antagonists of human IL-3 by the use of a cellular host expressing genes for the α- and β-chains of the human IL-3 receptor.

29 Claims, 2 Drawing Sheets

HUMAN INTERLEUKIN-3 RECEPTOR α SUBUNIT

The present application is the United States national application corresponding to International Application No. PCT/US 92/03026, filed Apr. 16, 1992 and designating the United States, which PCT application is in turn a continuation of U.S. application Ser. No. 07/688355, filed Apr. 19, 1991, now abandoned, the benefit of which applications are claimed pursuant to the provisions of 35 U.S.C. 120, 363 and 365 (C).

FIELD OF THE INVENTION

The invention relates generally to the human interleukin-3-receptor (hIL-3-receptor), and more particularly, to the synthesis of a human IL-3-receptor component and to the use of the receptor component for screening agonists and antagonists of human IL-3.

BACKGROUND

Circulating blood cells are constantly replaced by newly developed cells. Replacement blood cells are formed in a process termed hematopoiesis which involves the production of at least eight mature blood cell types within two major lineages: (1) the myeloid lineage which includes red blood cells (erythrocytes), macrophages (monocytes), eosinophilic granulocytes, megakaryocytes (platelets), neutrophilic granulocytes, basophilic granulocytes (mast cells); and (2) the lymphoid lineage which includes T lymphocytes, and B lymphocytes (Burgess and Nicola, Growth Factors and Stem Cells (Academic Press, New York, 1983)). Much of the control of blood cell formation is mediated by a group of interacting glycoproteins termed colony stimulating factors (CSFs), including G-CSF, M-CSF, GM-CSF, and multi-CSF (also known as IL-3). These glycoproteins are so named because of the in vivo and in vitro assays used to detect their presence. Techniques for the clonal culture of hematopoietic cells in semisolid culture medium have been especially important in the development of in vitro assays. In such cultures, individual progenitor cells (i.e., cells developmentally committed to a particular lineage, but still capable of proliferation) are able to proliferate to form a colony of maturing progeny in a manner which is believed to be essentially identical to the comparable process in vive. The role of CSFs in hematopoiesis is the subject of many reviews, and is of great interest to clinical investigators who must treat blood diseases or deficiencies: e.g. Metcalf, The Hemopoietic Colony Stimulating Factors (Elsevier, N.Y., 1984); Clark and Kamen, *Science*, Vol. 236, pgs. 1229–1237 (1987); Sachs,*Science*, Vol. 238, pgs. 1374–1379 (1987); Dexter et al., eds., Colony Stimulating Factors (Dekker, N.Y., 1990); and Morstyn et al., *Cancer Investigation*, Vol. 7, pgs. 443–456 (1989).

The biological effects of the CSFs are mediated by specific cell surface receptors, which may consist of one or more components. Recently, several of these have been cloned and characterized, e.g. Gearing et al., *EMBO J.*, Vol. 8, pgs. 3667–3676 (1989) (low affinity α-chain of human GM-CSF-receptor); Itoh et al., *Science*, Vol. 247, pgs. 324–327 (1990) (low affinity mouse IL-3-receptor); and Hayashida et al., *Proc. Natl. Acad. Sci.*, Vol. 87, pgs. 9655–9659 (1990) (β-chain of human GM-CSF-receptor). Besides contributing to an understanding of the signal transduction process, many of these receptors will be useful screening tools for agonists and antagonists of the natural ligand. In particular, such tools may lead to the development of non-protein agonists and antagonists which would obviate many of the difficulties associated with protein therapeutics, e.g. intravenous delivery, short serum half-life, and the like.

SUMMARY OF THE INVENTION

The invention is directed to a component of the human IL-3-receptor, referred to herein as the G-chain of the human IL-3-receptor, and to compositions thereof which bind with high affinity to human IL-3. Specifically such compositions include an α-chain and β-chain of the human IL-3-receptor that can operably associate to form a high affinity receptor for human IL-3. The invention includes allelic and genetically engineered variants of the α-chain-receptor, and nucleic acids encoding the α-chain-receptor and its allelic and genetically engineered variants. Preferably, the receptor component of the invention is selected from the group of polypeptides of the open reading frame defined by the amine acid sequence set forth in SEQ. ID. No. 2 (immediately preceding the Claims). Although the listed sequence includes the intracellular domain of the α-chain of the receptor, it is clear that truncated forms of the sequence which retain their extracellular and transmembrane domains and their ability of operably associate with the β-chain fall within the concept of the invention.

The invention is based in part on the discovery that high affinity binding of human IL-3 involves the same β-receptor component as high affinity binding of human GM-CSF. This led to the discovery and cloning of a cDNA clone, designated pDUK-1, which expresses a protein that is capable of binding to human IL-3 with high affinity when operably associated with the β-chain of a human IL-3-receptor (or equivalently a human GM-CSF-receptor), such as encoded by the cDNA insert of pKH97 deposited with the American Type Culture Collection (ATCC) (Rockville, Md.) under accession number 40847. pDUK-1 has been deposited with the ATCC under accession number 75001. The invention includes nucleic acids (i) that are effectively homologous to the cDNA insert of pDUK-1, and (ii) that encode proteins that form high affinity IL-3-receptors in association with the β-chain-receptor protein, e.g. as encoded by pKH97. As used herein, 'high affinity' in reference to IL-3-receptor binding means that IL-3 binds to the associated α- and β-chains of the receptor with a binding constant that is at least an order of magnitude less than that for binding to either component alone. More preferably. 'high affinity' means that IL-3 binds to the associated α- and β-chains of the receptor with a binding constant, $K_d$, less than 1 nM, and most preferably less than 200 pM.

DETAILED DESCRIPTION OF THE INVENTION

Figure 1:
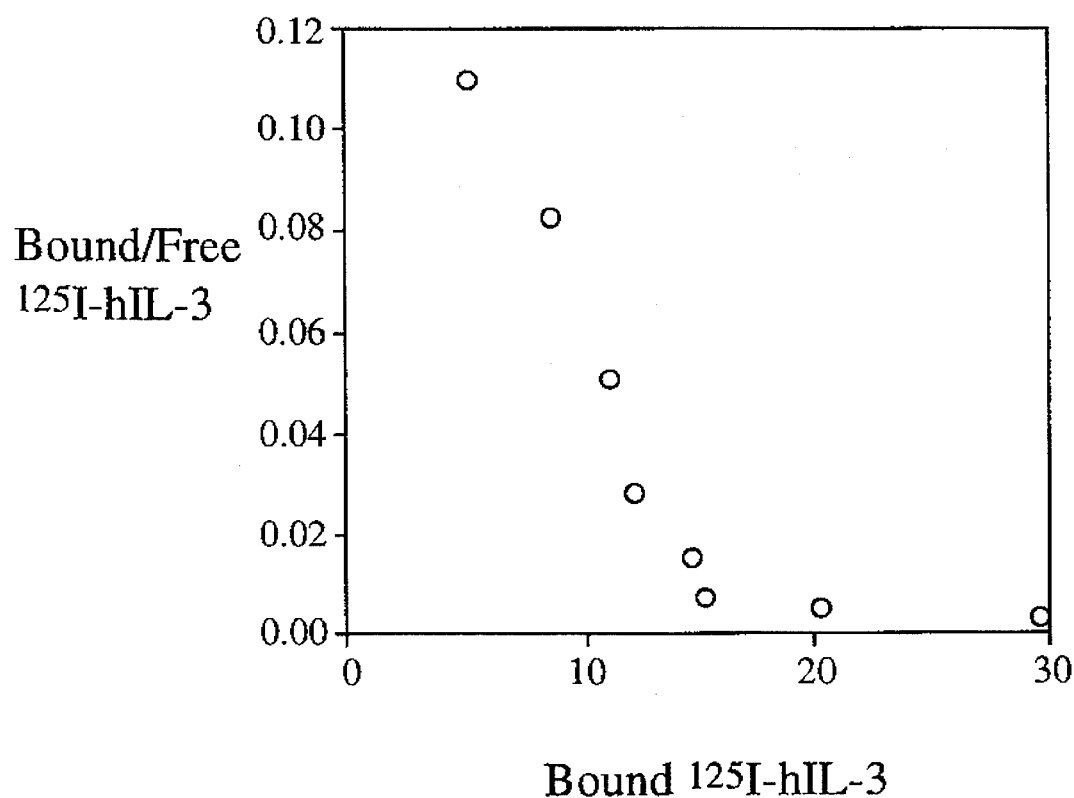
FIG. 1 illustrates the binding of $^{125}$I-labeled human IL-3 to COS 7 cells transiently co-transfected with KH97 and pDUK-1.

I. Obtaining and Expressing cDNAs for the Human IL-3-Receptor β-Chain

The term "effectively homologous" as used herein means that the nucleotide sequence is capable of being detected by a hybridization probe derived from a cDNA clone of the invention. The exact numerical measure of homology necessary to detect nucleic acids coding for a receptor α-chain depends on several factors including (1) the homology of the probe to coding sequences associated with the target nucleic acids that encode polypeptides other than the α-chain, (2) the stringency of the hybridization conditions, (3) the use of single-stranded or double-stranded probes, (4) the use of RNA or DNA probes, (5) the measures taken to reduce nonspecific binding of the probe, (6) the nature of the method used to label the probe, (7) the fraction of guanosine and cytidine nucleosides in the probe, (8) the distribution of mismatches between probe and target, (9) the size of the probe, and the like. Preferably, an effectively homologous nucleic acid sequence is at least seventy percent (70%) homologous to the cDNA of the invention. More preferably, an effectively homologous nucleic acid is at least ninety percent (90%) homologous to the cDNA of the invention. Most particularly, an effectively homologous nucleic acid sequence is one whose cDNA can be isolated by a probe based on the nucleic acid sequence set forth in SEQ. ID. NO. 1 using a standard hybridization protocol with no more than a few false positive signals, e.g. fewer than a hundred. There is an extensive literature that provides guidance in selecting conditions for such hybridizations: e.g. Hames et al., Nucleic Acid Hybridization: A Practical Approach (IRL Press, Washington, D.C., 1985); Gray et al., *Proc. Natl. Acad. Sci.*, Vol. 80, pgs. 5842–5846 (1983); Kafatos et al., *Nucleic Acids Research*, Vol. 7, pgs. 1541-1552 (1979); and Williams, *Genetic Engineering*, Vol. 1, pgs. 1–59 (1981), to name a few. By way of example, the nucleic acid of SEQ. ID. NO. 1 can be used as a probe in colony hybridization assays as described by Benton and Davis, *Science*, Vol. 196, pg. 180 (1977). Preferably, low stringency conditions are employed for the probe employed. (The dissociation temperature depends upon the probe length.) For example, for a probe of about 20–40 bases a typical prehybridization, hybridization, and wash protocol is as follows: (1) prehybridization: incubate nitrocellulose filters containing the denatured target DNA for 3–4 hours at 55° C. in 5× Denhardt's solution, 5× SSPE (20× SSPE consists of 174 g NaCl, 27.6 g $NaH_2PO_4.H_2O$, and 7.4 g EDTA in 800 ml $H_2O$ adjusted to pH 7.4 with 10N NaOH), 0.1% SDS, and 100 µg/ml denatured salmon sperm DNA, (2) hybridization: incubate filters in prehybridization solution plus probe at 55° C. for 2 hours, (3) wash: three 15 minute washes in 300–500 ml volumes of 6× SSC and 0.1% SDS at room temperature, followed by a final 1–1.5 minute wash in 300–500 ml of 1× SSC and 0.1% SDS at 55° C. Other equivalent procedures, e.g. employing organic solvents such as formamide, are well known in the art.

Homology as the term is used herein is a measure of similarity between two nucleotide (or amine add) sequences. Homology is expressed as the fraction or percentage of matching bases (or amine acids) after two sequences (possibly of unequal length) have been aligned. The term alignment is used in the sense defined by Sankoff and Kruskal in Chapter one of Time Warps, String Edits, and Macromolecules: The Theory and Practice of Sequence Comparison (Addison-Wesley, Reading, Mass., 1983). Roughly, two sequences are aligned by maximizing the number of matching bases (or amino adds) between the two sequences with the insertion of a minimal number of "blank" or "null" bases into either sequence to bring about the maximum overlap. Algorithms are available for computing the homology of two sequences: e.g. Needleham and Wunsch, *J. Mol. Biol.*, Vol. 48, pgs. 443–453 (1970); and Sankoff and Kruskal (cited above), pgs. 23–29. Also, commercial services and software packages are available for performing such comparisons, e.g. Intelligenetics, Inc. (Mountain View, Calif.); and University of Wisconsin Genetics Computer Group (Madison, Wis.).

Probes based on the nucleic acid sequence of the Sequence Listing can be synthesized on commercially available DNA synthesizers, e.g. Applied Biosystems model 381A, using standard techniques, e.g. Gait, Oligonucleotide Synthesis: A Practical Approach, (IRL Press, Washington D.C., 1984). It is preferable that the probe be at least 18–30 bases long. More preferably, the probe is at least 100–200 bases long. Probes of the invention can be labeled in a variety of ways standard in the art: e.g. radio-active labels, Berent et al., *Biotechniques*, pgs. 208–220 (May/June 1985), Meinkoth et al., *Anal. Biochem.*, Vol. 138, pgs. 267–284 (1984), Szostak et al., *Meth. Enzymol.*, Vol. 68, pgs. 419–429 (1979), and the like; and non-radioactive labels, Chu et al., *DNA*. Vol. 4, pgs. 327–331 (1985), Jablonski et al., *Nucleic Acids Research*, Vol. 14, pgs. 6115–6128 (1986), and the like.

Hybridization probes can also be used to screen candidate sources of α-chain mRNA prior to library construction, e.g. by RNA blotting, Maniatis et al., Molecular Cloning: A Laboratory Manual, pgs. 202–203 (Cold Spring Harbor Laboratory, N.Y., 1982); or Hames and Higgins, eds., pgs. 139–143 in Nucleic Adds Hybridization (IRL Press, Washington, D.C., 1985). Sources of mRNA encoding the desired polypeptides include cell populations or cell lines that express, or can be induced to express, large numbers of IL-3-receptors on their surfaces, e.g. in excess of 3000–5000.

Preferably, the α- and β-chains of the IL-3-receptor am co-transfected into a mammalian expression system (i.e. host-expression-vector combination). Many reviews are available which provide guidance for making choices and/or modifications of specific mammalian expression systems: e.g. (to name a few) Kucherlapati et al., *Critical Reviews in Biochemistry*, Vol. 16, Issue 4, pgs. 349–379 (1984), and Banerji et al., *Genetic Engineering*, Vol. 5, pgs. 19–31 (1983) review methods for transfecting and transforming mammalian cells; Reznikoff and Gold, eds., Maximizing Gene Expression (Butterworths, Boston, 1986) review selected topics in gene expression in *E. coli*, yeast, and mammalian cells; and Thilly, Mammalian Cell Technology (Butterworths, Boston, 1986) reviews mammalian expression systems. Likewise, many reviews are available which describe techniques and conditions for linking and/or manipulating specific cDNAs and expression control sequences to create and/or modify expression vectors suitable for use with the present invention, e.g. Maniatis et al., Molecular Cloning: A Laboratory Manual (Cold Spring Harbor Laboratory, N.Y., 1982); Glover, DNA Cloning: A Practical Approach, Vol. I and H (IRL Press, Oxford, 1985), and Perbal, A Practical Guide to Molecular Cloning (John Wiley & Sons, New York, 1984), to name only a few.

Several DNA tumor viruses have been used as vectors for mammalian hosts. Particularly important are the numerous vectors which comprise SV40 replication, transcription, and/or translation control sequences coupled to bacterial replication control sequences, e.g. the pcD vectors developed by Okayama and Berg, disclosed in *Mol. Cell Biol.*, Vol. 2, pgs. 161–170 (1982) and in *Mol. Cell Biol.*, Vol. 3, pgs. 280–289 (1983), both of which are incorporated herein by reference; the SV40 vectors disclosed by Hamer in *Genetic Engineering*, Vol. 2, pgs. 83–100 (1980), and in U.S. Pat. 4,599,308, both of which are incorporated herein by reference; and the vectors additionally containing adenovirus regulatory elements, disclosed by Kaufman and Sharp in *Mol. Cell Biol.*, Vol. 2, pgs. 1304–1319 (1982), and by Clark et al. in U.S. Pat. 4,675,285, both of which are incorporated herein by reference. COS7 monkey cells, described by Gluzman, *Cell*, Vol. 23, pgs. 175–182 (1981) and available from the ATCC (accession no. CRL 1651), are usually the preferred hosts for the above vectors. SV40-based vectors suitable for mammalian-receptor expression have been developed by Aruffo and Seed, *Proc. Natl. Acad. Sci.*, Vol. 84, pgs. 3365–3369 and 8573–8577 (1987).

II. Binding Assays

Binding assays are accomplished by letting a ligand of unknown specificity or affinity compete with a known amount or concentration of labeled human IL-3 for receptor-binding sites of a sample of cells transfected or transformed with pDUK-1, or its equivalent. Preferably, the IL-3 is labeled by radioiodination using standard protocols, e.g. reaction with 1,3,4,6-tetrachloro-3α, 6β-diphenylglycouril described by Fraker et al., *Biochem. Biophys. Res. Commun.*, Vol. 80, pgs. 849–857 (1978) (and available from Pierce Chemical Co. as Iodogen). Generally, the binding assay is conducted as described by Lowenthal et al., *J. Immunol.*, Vol 140, pgs. 456–464 (1988), which is incorporated by reference. Briefly, aliquots of cells are incubated in the presence of $^{125}$I-labeled human IL-3 in a final volume of 200 µl culture medium in microfuge tubes at 4° C. Cell-bound $^{125}$I-labeled IL-3 was separated from non-bound $^{125}$I-labeled IL-3 by centrifugation through an oil gradient (10,000× G for 2 min). Nonspecific binding is measured in the presence of a 100-fold excess of partially purified unlabeled human IL-3.

The following Examples illustrate but do not limit the invention:

EXAMPLES

Example I

Construction of cDNA library from TF-1 cells and isolation of pDUK-1

Figure 2:
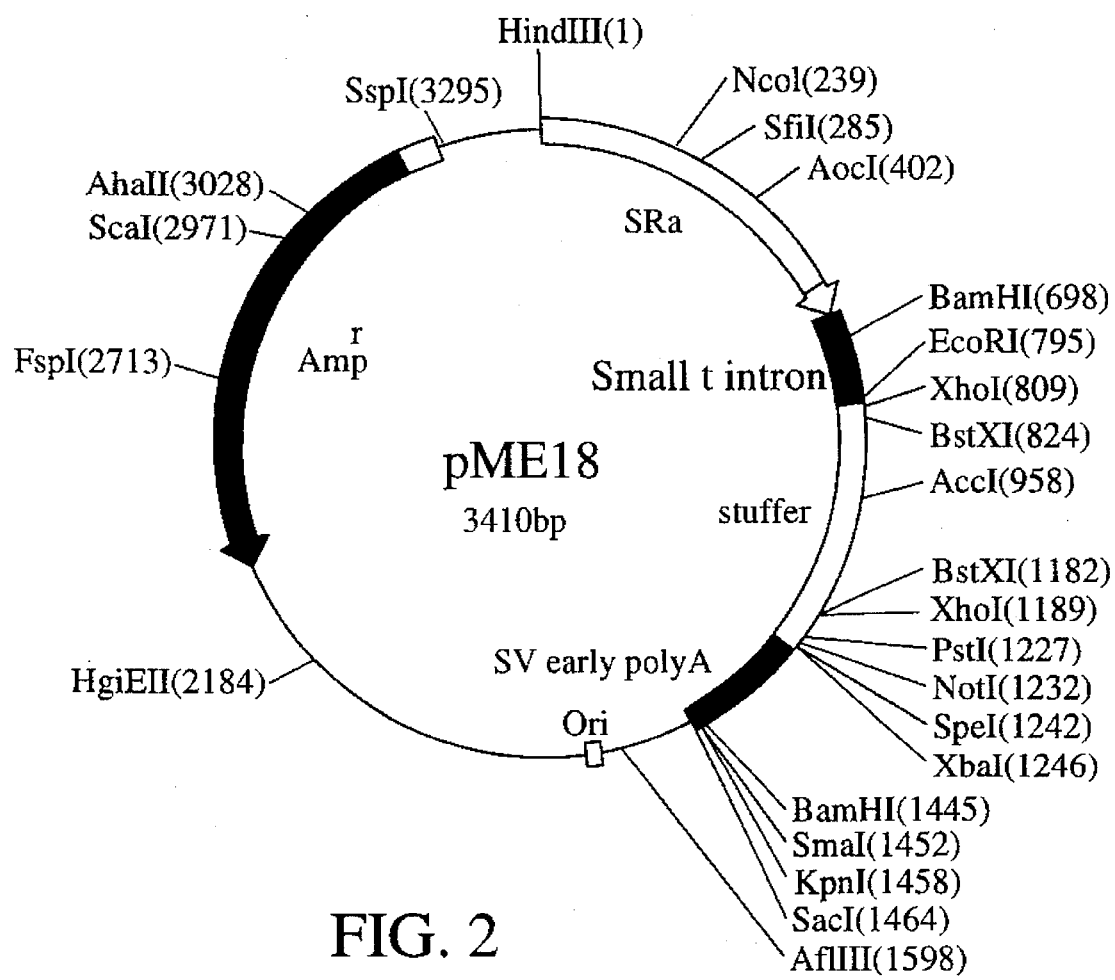
FIG. 2 is a restriction map of the vector pME 18.

Poly(A)$^+$RNA from human TF-1 cells (Kitamura et al., *J. Cell Physiol.*, Vol. 140, pgs. 323–334 (1989)) cultured in the presence of hIL-3 (5 ng/ml) was isolated by the guanidium isothiocyanate method (Chirgwin et al., *Biochemistry*, Vol. 18, pgs. 5294–5299 (1978)), and was converted to double-stranded cDNA using oligo(dT) primers. After Bst XI linkers (containing Xba I sites) were ligated to both ends of the cDNAs, the cDNAs were size-fractionated through an agarose gel. cDNAs greater than 1.0 kb were digested with Xba I and ligated with Xba I-digested pME 18, an SV40-based mammalian expression vector, diagrammed in FIG. 2, to form a library of about 3×10$^6$ independent clones. About 3 µg of miniprep DNA from pools of 3×10$^3$ clones was co-transfected with 50 ng of pKH97 (carrying a cDNA insert encoding the β-chain of the hGM-CSF-receptor) into COS 7 cells by electroporation (0.4 gap cuvette at 300 volts and 300 µF using a Gene Pulser (BioRad, Richmond, Calif.)). The Cos 7 cells were incubated for 72 hours prior to screening. pDUK-1 was isolated by screening for cells capable of high affinity binding to $^{125}$I-labelled hIL-3. 10 nM $^{125}$I-labelled hIL-3 was added to transfected Cos 7 cells in a Chamber Slide (Labo-Tek), after which cells binding $^{125}$I-labelled hIL-3 were identified by microscopic autoradiography.

Example II

Binding of hIL-3 to COS 7 cells Co-transfected with pKH97 and pDUK-1

A total of 5 µg of equal amounts of pKH97 and pDUK-1 plasmid DNA was transfected into semi-confluent COS 7 cells by the DEAE-dextran method. 72 hours after transfection, the cells were harvested and analyzed in IL-3 binding assays. Duplicates of 2×10$^5$ COS 7 cells in 0.1 ml of RPMI 1640 containing 10% fetal calf serum, 2 mM EDTA, 0.02% sodium azide and 20 mM Hepes (pH 7.4) were incubated for 3 hours at 4° C. with various concentrations of $^{125}$I-labeled human IL-3 with or without an excess amount of non-labeled human IL-3. The cell-bound radioactivity was measured by separating the cells from free ligand by centrifugation through an oil layer, as described by Schreurs et al., *Growth Factors*, Vol. 2, pgs. 221–233 (1990). IL-3 was iodinated by a standard protocol, that of Chiba et al., *Leukemia*, Vol. 4, pgs. 22–36 (1990). Briefly, 5 µg of *E. coli*-produced human IL-3 was incubated in 30–50 µl of 50 mM sodium borate buffer (pH 8.0) with 1 mCi of the dried Bolton and Hunter reagent for 12–16 hours at 4° C. Glycine was added to 2.5 mg/ml to stop the reaction and the iodinated IL-3 was separated from the free Bolton and Hunter reagent by a PD-10 column. The iodinated human IL-3 had a specific radioactivity of (4 to 8)×10$^7$ cpm/µg and was stable for about two months in Hepes-buffered Hanks's balanced salt solution containing 0.1% gelatin, 0.1% bovine serum albumin, and 0.02% sodium azide.

FIG. 1 shows the receptor-binding data. Open circles correspond to COS 7 calls transfected with pKH125 and pKH97. Scatchard analysis (by the LIGAND program, De Lean et al., *Mol. Pharmacol.*, Vol. 21, pgs. 5–16 (1982)) of the binding data indicated an equilibrium binding constant, $K_d$, of 100 pM.

Example III

Co-transfection of pKH97 and pDUK-1 into NIH3T3 Cells

A DNA fragment containing the neomycin-resistance gene, neo, was inserted into pKH97 downstream of the SRα promoter to form pKH97neo, and a DNA fragment containing the hygromycin-resistance gene, hyg, was inserted into pDUK-1 downstream of the SRα promoter to form pDUK-1 hyg. NIH3T3 calls were stably transfected with pKH97neo and pDUK-1 hyg by the calcium-phosphate procedure, described by Chen and Okayama, *Mol. Cell Biol.*, Vol. 7, pgs. 2745–2752 (1987), which reference is incorporated by reference. Stable co-transfectants were selected by 1 mg/ml of G418 and 1 mg/ml hygromycin. Analysis of the binding of $^{125}$I-labelled hIL-3 indicated a $K_d$ of about 100 pM.

Example IV.

Use of Stably Co-transfected NIH3T3 cells to screen for IL-3 Antagonists

Aliquots of NIH3T3 cells co-transfected with pKH97neo and pDUK-1 hyg as described above are distributed to wells of microtiter plates in 200 µl of medium containing $^{125}$I- labeled human IL-3 at concentrations of 100 pM, 500 pM, and 1 nM. 100 μl samples of microbial supernatants free of cells are added to the transfected NIH3T3 cells at each of the different concentrations of $^{125}$I-labeled IL-3. After incubation for 3 hours the NIH3T3 cells are harvested and assayed for bound radioactivity. NIH3T3 cells with low counts of bound radioactivity correspond to microbial samples containing candidate antagonists or agonists of human IL-3.

The descriptions of the foregoing embodiments of the invention have been presented for purpose of illustration and description. They are not intended to be exhaustive or to limit the invention to the precise forms disclosed, and obviously many modifications and variations are possible in light of the above teaching. The embodiments were chosen and described in order to best explain the principles of the invention to thereby enable others skilled in the art to best utilize the invention in various embodiments and with various modifications as are suited to the particular use contemplated. It is intended that the scope of the invention be defined by the claims appended hereto.

Applicants have deposited pKH97 and pDUK-1 with the American Type Culture Collection, Rockville, Md., USA (ATCC), under accession numbers 40847 and 75001, respectively. These deposits were made under conditions as provided under ATCC's agreement for Culture Deposit for Patent Purposes, which assures that the deposit will be made available to the US Commissioner of Patents and Trademarks pursuant to 35 USC 122 and 37 CFR 1.14, and will be made available to the public upon issue of a U.S. patent, which requires that the deposit be maintained. Availability of the deposited plasmids is not to be construed as a license to practice the invention in contravention of the rights granted under the authority of any government in accordance with its patent laws.

The Deposits have been modified to satisfy the requirements of the Budapest Treaty on the Deposit of Microorganisms.

We claim:

1. Human IL3 receptor α-chain subunit substantially free of other human proteins.

2. The α-chain subunit of claim 1 comprising SEQ ID NO: 2.

3. The α-chain subunit of claim 1, capable of forming an operable association with a β-chain of a human interleukin-3 receptor.

4. The α-chain subunit of claim 3, wherein said operable association provides for binding human IL-3 with a binding constant at least an order of magnitude less than by either α-chain or β-chain alone.

5. The α-chain subunit of claim 1, which is a recombinant protein.

6. The α-chain subunit of claim 5, made in *E. coli*, yeast, or a mammalian cell.

7. A method of identifying an IL-3 receptor ligand, said method comprising the steps of:
   expressing a recombinant gene for human IL-3 receptor α-chain subunit, and a gene for β-chain of interleukin-3-receptor so that said α- and β-chain operably associate to form a high affinity interleukin-3-receptor;
   contacting said IL-3 receptor with a sample comprising a putative ligand for said receptor; and
   determining whether said putative ligand affects binding of IL-3 to said high affinity receptor for IL-3.

8. The method of claim 7, wherein said ligand is an agonist or antagonist of said receptor.

9. The method of claim 7 wherein said expressing is in a cell.

10. The method of claim 9 wherein said cell is stably transformed with a first vector carrying said gene for α-chain and a second vector carrying said gene for β-chain.

11. The method of claim 10 wherein said first vector is pDUK-1, said second vector is pKH97 and said high affinity interleukin-3-receptor has a binding constant with human interleukin-3 of less than 1 nM.

12. The method of claim 9, wherein said cell is *E. coli*, yeast, or a mammalian cell.

13. The method of claim 7, wherein said α-chain comprises SEQ ID NO: 2.

14. The method of claim 13, wherein said gone comprises SEQ ID NO:1.

15. A composition of matter comprising a recombinant human IL-3 receptor α-subunit and a β-chain of an interleukin-3-receptor, said α-chain subunit and β-chain being in operable association.

16. The composition of matter of claim 15 wherein said α-chain subunit is encoded by the cDNA insert of pDUK-1 and said β-chain is encoded by the cDNA insert of pKH97.

17. The composition of claim 5, wherein said composition binds human interleukin-3 with a binding constant at least an order of magnitude less than by either α-chain or β-chain alone.

18. The composition of claim 17, wherein said composition provides a binding constant of less than 1 nM.

19. The composition of claim 18, wherein said binding constant is less than 200 pM.

20. The α-chain subunit of claim 15, comprising SEQ ID NO: 2.

21. The α-chain subunit of claim 15, wherein said subunit is a recombinant protein.

22. The α-chain subunit of claim 21, made in *E. coli*, yeast, or a mammalian cell.

23. A cell comprising a composition of claim 15.

24. The cell of claim 23, wherein said operable association confers IL-3 responsiveness onto said cell.

25. A recombinant polypeptide comprising SEQ ID NO: 2.

26. The polypeptide of claim 25, made by expressing a nucleic acid comprising SEQ ID NO: 1.

27. A cell comprising a polypeptide of claim 26.

28. The cell of claim 27, which is *E. coli*, yeast, or a mammalian cell.

29. A method of determining the effect on an IL-3 receptor by a reagent, said method comprising the steps of:
   combining a polypeptide of claim 25 with a β-chain of an interleukin-3-receptor so that said α- and β-chain gene products operably associate to form a high affinity interleukin-3-receptor; and
   measuring the effect of said reagent on said high affinity receptor for IL-3.

* * * * *

SEQUENCE LISTING ( 1 ) GENERAL INFORMATION:

( i i i ) NUMBER OF SEQUENCES:2

( 2 ) INFORMATION FOR SEQ ID NO:1:

( i ) SEQUENCE CHARACTERISTICS:
      ( A ) LENGTH: 1460 bases
      ( B ) TYPE: Nucleic acid
      ( C ) STRANDEDNESS: single
      ( D ) TOPOLOGY: linear ( i i ) MOLECULE TYPE: DNA ( v i ) ORIGINAL SOURCE:
      ( A ) ORGANISM: Homo sapiens ( i x ) FEATURE:
      ( D ) OTHER INFORMATION: Encodes Human IL-3-receptor ( x i ) SEQUENCE DESCRIPTION: SEQ ID NO:1:

```
GCACACGGGA  AGATATCAGA  AACATCCTAG  GATCAGGACA  CCCCAGATCT  TCTCAACTGG   60

AACCACGAAG  GCTGTTTCTT  CCACACAGCA  CTTTGATCTC  CATTTAAGCA  GGCACCTCTG  120

TCCTGCGTTC  CGGAGCTGCG  TTCCCG ATG  GTC  CTC  CTT  TGG  CTC  ACG  CTG  CTC  173
                               Met  Val  Leu  Leu  Trp  Leu  Thr  Leu  Leu
                                                                    - 15

CTG  ATC  GCC  CTG  CCC  TGT  CTC  CTG  CAA  ACG  AAG  GAA  GAT  CCA  AAC  CCA   221
Leu  Ile  Ala  Leu  Pro  Cys  Leu  Leu  Gln  Thr  Lys  Glu  Asp  Pro  Asn  Pro
- 10                 - 5                        1                     5

CCA  ATC  ACG  AAC  CTA  AGG  ATG  AAA  GCA  AAG  GCT  CAG  CAG  TTG  ACC  TGG   269
Pro  Ile  Thr  Asn  Leu  Arg  Met  Lys  Ala  Lys  Ala  Gln  Gln  Leu  Thr  Trp
                10                  15                       20

GAC  CTT  AAC  AGA  AAT  GTG  ACC  GAT  ATC  GAG  TGT  GTT  AAA  GAT  GCC  GAC   317
Asp  Leu  Asn  Arg  Asn  Val  Thr  Asp  Ile  Glu  Cys  Val  Lys  Asp  Ala  Asp
          25                       30                        35

TAT  TCT  ATG  CCG  GCA  GTG  AAC  AAT  AGC  TAT  TGC  CAG  TTT  GGA  GCA  ATT   365
Tyr  Ser  Met  Pro  Ala  Val  Asn  Asn  Ser  Tyr  Cys  Gln  Phe  Gly  Ala  Ile
     40                       45                       50

TCC  TTA  TGT  GAA  GTG  ACC  AAC  TAC  ACC  GTC  CGA  GTG  GCC  AAC  CCA  CCA   413
Ser  Leu  Cys  Glu  Val  Thr  Asn  Tyr  Thr  Val  Arg  Val  Ala  Asn  Pro  Pro
```

```
     55                    60                    65                    70
TTC  TCC  ACG  TGG  ATC  CTC  TTC  CCT  GAG  AAC  AGT  GGG  AAG  CCT  TGG  GCA        461
Phe  Ser  Thr  Trp  Ile  Leu  Phe  Pro  Glu  Asn  Ser  Gly  Lys  Pro  Trp  Ala
               75                        80                        85

GGT  GCG  GAG  AAT  CTG  ACC  TGC  TGG  ATT  CAT  GAC  GTG  GAT  TTC  TTG  AGC        509
Gly  Ala  Glu  Asn  Leu  Thr  Cys  Trp  Ile  His  Asp  Val  Asp  Phe  Leu  Ser
               90                        95                       100

TGC  AGC  TGG  GCG  GTA  GGC  CCG  GGG  GCC  CCC  GCG  GAC  GTC  CAG  TAC  GAC        557
Cys  Ser  Trp  Ala  Val  Gly  Pro  Gly  Ala  Pro  Ala  Asp  Val  Gln  Tyr  Asp
              105                       110                       115

CTG  TAC  TTG  AAC  GTT  GCC  AAC  AGG  CGT  CAA  CAG  TAC  GAG  TGT  CTT  CAC        605
Leu  Tyr  Leu  Asn  Val  Ala  Asn  Arg  Arg  Gln  Gln  Tyr  Glu  Cys  Leu  His
              120                       125                       130

TAC  AAA  ACG  GAT  GCT  CAG  GGA  ACA  CGT  ATC  GGG  TGT  CGT  TTC  GAT  GAC        653
Tyr  Lys  Thr  Asp  Ala  Gln  Gly  Thr  Arg  Ile  Gly  Cys  Arg  Phe  Asp  Asp
135                       140                       145                       150

ATC  TCT  CGA  CTC  TCC  AGC  GGT  TCT  CAA  AGT  TCC  CAC  ATC  CTG  GTG  CGG        701
Ile  Ser  Arg  Leu  Ser  Ser  Gly  Ser  Gln  Ser  Ser  His  Ile  Leu  Val  Arg
              155                       160                       165

GGC  AGG  AGC  GCA  GCC  TTC  GGT  ATC  CCC  TGC  ACA  GAT  AAG  TTT  GTC  GTC        749
Gly  Arg  Ser  Ala  Ala  Phe  Gly  Ile  Pro  Cys  Thr  Asp  Lys  Phe  Val  Val
              170                       175                       180

TTT  TCA  CAG  ATT  GAG  ATA  TTA  ACT  CCA  CCC  AAC  ATG  ACT  GCA  AAG  TGT        797
Phe  Ser  Gln  Ile  Glu  Ile  Leu  Thr  Pro  Pro  Asn  Met  Thr  Ala  Lys  Cys
              185                       190                       195

AAT  AAG  ACA  CAT  TCC  TTT  ATG  CAC  TGG  AAA  ATG  AGA  AGT  CAT  TTC  AAT        845
Asn  Lys  Thr  His  Ser  Phe  Met  His  Trp  Lys  Met  Arg  Ser  His  Phe  Asn
200                       205                       210

CGC  AAA  TTT  CGC  TAT  GAG  CTT  CAG  ATA  CAA  AAG  AGA  ATG  CAG  CCT  GTA        893
Arg  Lys  Phe  Arg  Tyr  Glu  Leu  Gln  Ile  Gln  Lys  Arg  Met  Gln  Pro  Val
215                       220                       225                       230

ATC  ACA  GAA  CAG  GTC  AGA  GAC  AGA  ACC  TCC  TTC  CAG  CTA  CTC  AAT  CCT        941
Ile  Thr  Glu  Gln  Val  Arg  Asp  Arg  Thr  Ser  Phe  Gln  Leu  Leu  Asn  Pro
              235                       240                       245

GGA  ACG  TAC  ACA  GTA  CAA  ATA  AGA  GCC  CGG  GAA  AGA  GTG  TAT  GAA  TTC        989
Gly  Thr  Tyr  Thr  Val  Gln  Ile  Arg  Ala  Arg  Glu  Arg  Val  Tyr  Glu  Phe
              250                       255                       260

TTG  AGC  GCC  TGG  AGC  ACC  CCC  CAG  CGC  TTC  GAG  TGC  GAC  CAG  GAG  GAG       1037
Leu  Ser  Ala  Trp  Ser  Thr  Pro  Gln  Arg  Phe  Glu  Cys  Asp  Gln  Glu  Glu
              265                       270                       275

GGC  GCA  AAC  ACA  CGT  GCC  TGG  CGG  ACG  TCG  CTG  CTG  ATC  GCG  CTG  GGG       1085
Gly  Ala  Asn  Thr  Arg  Ala  Trp  Arg  Thr  Ser  Leu  Leu  Ile  Ala  Leu  Gly
              280                       285                       290

ACG  CTG  CTG  GCC  CTG  GTC  TGT  GTC  TTC  GTG  ATC  TGC  AGA  AGG  TAT  CTG       1133
Thr  Leu  Leu  Ala  Leu  Val  Cys  Val  Phe  Val  Ile  Cys  Arg  Arg  Tyr  Leu
295                       300                       305                       310

GTG  ATG  CAG  AGA  CTC  TTT  CCC  CGC  ATC  CCT  CAC  ATG  AAA  GAC  CCC  ATC       1181
Val  Met  Gln  Arg  Leu  Phe  Pro  Arg  Ile  Pro  His  Met  Lys  Asp  Pro  Ile
              315                       320                       325

GGT  GAC  AGC  TTC  CAA  AAC  GAC  AAG  CTG  GTG  GTC  TGG  GAG  GCG  GGC  AAA       1229
Gly  Asp  Ser  Phe  Gln  Asn  Asp  Lys  Leu  Val  Val  Trp  Glu  Ala  Gly  Lys
              330                       335                       340

GCC  GGC  CTG  GAG  GAG  TGT  CTG  GTG  ACT  GAA  GTA  CAG  GTC  GTG  CAG  AAA       1277
Ala  Gly  Leu  Glu  Glu  Cys  Leu  Val  Thr  Glu  Val  Gln  Val  Val  Gln  Lys
              345                       350                       355

ACT  TGAGACTGGG GTTCAGGGCT TGTGGGGGTC TGCCTCAATC TCCCTGGCCG                          1330
Thr

GGCCAGGCGC CTGCACAGAC TGGCTGCTGG ACCTGCGCAC GCAGCCCAGG                               1380

AATGGACATT CCTAACGGGT GGCCTGTGTA ATTTCGTTGG GCATGGGAGA                               1430
```

TGCCGAAGCT GCCAGGAAGA AGAACAGAAC 1460

( 2 ) INFORMATION FOR SEQ ID NO:2:

( i ) SEQUENCE CHARACTERISTICS:
        ( A ) LENGTH: 378 amino acid residues
        ( B ) TYPE: amino acid
        ( C ) STRANDEDNESS: single
        ( D ) TOPOLOGY: linear ( i i ) MOLECULE TYPE: protein ( v i ) ORIGINAL SOURCE:
        ( A ) ORGANISM: Homo sapiens ( i x ) FEATURE:
        ( D ) OTHER INFORMATION: Human IL-3- receptor ( x i ) SEQUENCE DESCRIPTION: SEQ ID NO:2:

```
Met   Val   Leu   Leu   Trp   Leu   Thr   Leu   Leu   Ile   Ala   Leu   Pro   Cys   Leu
                  -15                 -10                              -5

Leu   Gln   Thr   Lys   Glu   Asp   Pro   Asn   Pro   Pro   Ile   Thr   Asn   Leu   Arg   Met
                   1                  5                              10

Lys   Ala   Lys   Ala   Gln   Gln   Leu   Thr   Trp   Asp   Leu   Asn   Arg   Asn   Val   Thr
             15                  20                              25

Asp   Ile   Glu   Cys   Val   Lys   Asp   Ala   Asp   Tyr   Ser   Met   Pro   Ala   Val   Asn
 30                              35                  40                              45

Asn   Ser   Tyr   Cys   Gln   Phe   Gly   Ala   Ile   Ser   Leu   Cys   Glu   Val   Thr   Asn
                         50                        55                              60

Tyr   Thr   Val   Arg   Val   Ala   Asn   Pro   Pro   Phe   Ser   Thr   Trp   Ile   Leu   Phe
                   65                  70                              75

Pro   Glu   Asn   Ser   Gly   Lys   Pro   Trp   Ala   Gly   Ala   Glu   Asn   Leu   Thr   Cys
             80                  85                              90

Trp   Ile   His   Asp   Val   Asp   Phe   Leu   Ser   Cys   Ser   Trp   Ala   Val   Gly   Pro
       95                        100                       105

Gly   Ala   Pro   Ala   Asp   Val   Gln   Tyr   Asp   Leu   Tyr   Leu   Asn   Val   Ala   Asn
110                              115                       120                            125

Arg   Arg   Gln   Gln   Tyr   Glu   Cys   Leu   His   Tyr   Lys   Thr   Asp   Ala   Gln   Gly
                  130                       135                             140

Thr   Arg   Ile   Gly   Cys   Arg   Phe   Asp   Asp   Ile   Ser   Arg   Leu   Ser   Ser   Gly
                  145                       150                             155

Ser   Gln   Ser   Ser   His   Ile   Leu   Val   Arg   Gly   Arg   Ser   Ala   Ala   Phe   Gly
             160                       165                             170

Ile   Pro   Cys   Thr   Asp   Lys   Phe   Val   Val   Phe   Ser   Gln   Ile   Glu   Ile   Leu
      175                       180                       185

Thr   Pro   Pro   Asn   Met   Thr   Ala   Lys   Cys   Asn   Lys   Thr   His   Ser   Phe   Met
190                              195                       200                            205

His   Trp   Lys   Met   Arg   Ser   His   Phe   Asn   Arg   Lys   Phe   Arg   Tyr   Glu   Leu
                  210                       215                             220

Gln   Ile   Gln   Lys   Arg   Met   Gln   Pro   Val   Ile   Thr   Glu   Gln   Val   Arg   Asp
             225                       230                             235

Arg   Thr   Ser   Phe   Gln   Leu   Leu   Asn   Pro   Gly   Thr   Tyr   Thr   Val   Gln   Ile
             240                       245                             250

Arg   Ala   Arg   Glu   Arg   Val   Tyr   Glu   Phe   Leu   Ser   Ala   Trp   Ser   Thr   Pro
      255                       260                       265

Gln   Arg   Phe   Glu   Cys   Asp   Gln   Glu   Glu   Gly   Ala   Asn   Thr   Arg   Ala   Trp
270                              275                       280                            285

Arg   Thr   Ser   Leu   Leu   Ile   Ala   Leu   Gly   Thr   Leu   Leu   Ala   Leu   Val   Cys
```

|  |  |  | | 290 | | | | | 295 | | | | | 300 | |
|---|---|---|---|---|---|---|---|---|---|---|---|---|---|---|---|
| Val | Phe | Val | Ile 305 | Cys | Arg | Arg | Tyr | Leu 310 | Val | Met | Gln | Arg | Leu 315 | Phe | Pro |
| Arg | Ile | Pro 320 | His | Met | Lys | Asp | Pro 325 | Ile | Gly | Asp | Ser | Phe 330 | Gln | Asn | Asp |
| Lys | Leu 335 | Val | Val | Trp | Glu | Ala 340 | Gly | Lys | Ala | Gly | Leu 345 | Glu | Glu | Cys | Leu |
| Val 350 | Thr | Glu | Val | Gln | Val 355 | Val | Gln | Lys | Thr | | | | | | |